US009561117B2

(12) United States Patent
Lechmann et al.

(10) Patent No.: US 9,561,117 B2
(45) Date of Patent: Feb. 7, 2017

(54) EXPANDABLE IMPLANT

(71) Applicant: DePuy Synthes Products, Inc., Raynham, MA (US)

(72) Inventors: Beat Lechmann, Oberdorf (CH); Dominique Burkard, Gretzenbach (CH); Michael Schwager, Winterthur (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/569,105

(22) Filed: Dec. 12, 2014

(65) Prior Publication Data

US 2015/0094813 A1    Apr. 2, 2015

Related U.S. Application Data

(63) Continuation of application No. 13/784,955, filed on Mar. 5, 2013, now Pat. No. 8,940,052.
(Continued)

(51) Int. Cl.
*A61F 2/44* (2006.01)
*A61F 2/46* (2006.01)
(Continued)

(52) U.S. Cl.
CPC ............. *A61F 2/447* (2013.01); *A61F 2/441* (2013.01); *A61F 2/442* (2013.01); *A61F 2/4611* (2013.01);
(Continued)

(58) Field of Classification Search
CPC .... A61F 2/44; A61F 2/441; A61F 2002/4415; A61F 2/4611
(Continued)

(56) References Cited

U.S. PATENT DOCUMENTS 4,349,921 A    9/1982  Kuntz
4,863,476 A    9/1989  Shepperd
(Continued)

FOREIGN PATENT DOCUMENTS

CN    101909548 A    12/2010
DE    4012622    7/1997
(Continued)

OTHER PUBLICATIONS

Gore, Technique of Cervical Interbody Fusion, Clinical Orthopaedics and Related Research, Sep. 1984, pp. 191-195, No. 188.
(Continued)

*Primary Examiner* — Ellen C Hammond
*Assistant Examiner* — Christina Negrellirodrigue
(74) *Attorney, Agent, or Firm* — Baker & Hostetler LLP

(57) ABSTRACT

An expandable implant for inserting within a skeletal space is provided, and a method for using the implant to expand the skeletal space. The implant is preferably designed to be inserted into an intervertebral space to replace at least part of an intervertebral disc between adjacent vertebral bodies. The expandable implant contains at least one first expansion compartment and at least one second expansion compartments, which compartments can be inflatable balloons that are inflated by a catheter. Inflating the first expansion compartment expands the implant in a first direction and inflating the second expansion compartment expands the implant in a second direction.

21 Claims, 8 Drawing Sheets

Related U.S. Application Data

(60) Provisional application No. 61/675,975, filed on Jul. 26, 2012.

(51) Int. Cl.
   *A61F 2/30* (2006.01)
   *A61F 2/48* (2006.01)

(52) U.S. Cl.
   CPC ............. *A61F 2002/30019* (2013.01); *A61F 2002/3055* (2013.01); *A61F 2002/30179* (2013.01); *A61F 2002/30359* (2013.01); *A61F 2002/30467* (2013.01); *A61F 2002/30505* (2013.01); *A61F 2002/30537* (2013.01); *A61F 2002/30556* (2013.01); *A61F 2002/30579* (2013.01); *A61F 2002/30581* (2013.01); *A61F 2002/30583* (2013.01); *A61F 2002/30586* (2013.01); *A61F 2002/30828* (2013.01); *A61F 2002/30836* (2013.01); *A61F 2002/30909* (2013.01); *A61F 2002/30912* (2013.01); *A61F 2002/484* (2013.01); *A61F 2310/00017* (2013.01); *A61F 2310/00023* (2013.01); *A61F 2310/00029* (2013.01); *A61F 2310/00047* (2013.01); *A61F 2310/00101* (2013.01); *A61F 2310/00359* (2013.01); *A61F 2310/00407* (2013.01); *A61F 2310/00796* (2013.01)

(58) Field of Classification Search
   USPC ................ 606/246–249; 623/17.11–17.16
   See application file for complete search history.

(56) References Cited

U.S. PATENT DOCUMENTS

| | | |
|---|---|---|
| 5,059,193 A | 10/1991 | Kuslich |
| 5,290,312 A | 3/1994 | Kojimoto et al. |
| 5,344,252 A | 9/1994 | Kakimoto |
| 5,370,697 A | 12/1994 | Baumgartner |
| 5,390,683 A | 2/1995 | Pishardi |
| 5,443,514 A | 8/1995 | Steffee |
| 5,522,899 A | 6/1996 | Michelson |
| 5,534,029 A | 7/1996 | Shima |
| 5,554,191 A | 9/1996 | Lahille et al. |
| 5,609,635 A | 3/1997 | Michelson |
| 5,653,763 A | 8/1997 | Errico |
| 5,658,335 A | 8/1997 | Allen |
| 5,665,122 A | 9/1997 | Kambin |
| 5,697,977 A | 12/1997 | Pisharodi |
| 5,716,415 A | 2/1998 | Steffee |
| 5,772,661 A | 6/1998 | Michelson |
| 5,782,832 A | 7/1998 | Larsen et al. |
| 5,860,973 A | 1/1999 | Michelson |
| 5,865,848 A | 2/1999 | Baker |
| 5,888,224 A | 3/1999 | Beckers et al. |
| 5,893,889 A | 4/1999 | Harrington |
| 5,893,890 A | 4/1999 | Pisharodi |
| 5,980,522 A | 11/1999 | Koros et al. |
| 6,039,761 A | 3/2000 | Li |
| 6,045,579 A | 4/2000 | Hochshuler |
| 6,102,950 A | 8/2000 | Vaccaro |
| 6,106,557 A | 8/2000 | Robioneck et al. |
| 6,117,174 A | 9/2000 | Nolan |
| 6,127,597 A | 10/2000 | Beyar et al. |
| 6,129,763 A | 10/2000 | Chauvin et al. |
| 6,146,387 A | 11/2000 | Trott et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley et al. |
| 6,296,647 B1 | 10/2001 | Robioneck et al. |
| 6,302,914 B1 | 10/2001 | Michelson |
| 6,332,895 B1 | 12/2001 | Suddaby |
| 6,368,351 B1 | 4/2002 | Glenn |
| 6,375,682 B1 | 4/2002 | Fleischmann et al. |
| 6,387,130 B1 | 5/2002 | Stone |
| 6,409,766 B1 | 6/2002 | Brett |
| 6,419,705 B1 | 7/2002 | Erickson |
| 6,419,706 B1 | 7/2002 | Graf |
| 6,436,140 B1 | 8/2002 | Liu et al. |
| 6,454,806 B1 | 9/2002 | Cohen et al. |
| 6,454,807 B1 | 9/2002 | Jackson |
| 6,488,710 B2 | 12/2002 | Besselink |
| 6,527,804 B1 | 3/2003 | Gauchet et al. |
| 6,558,424 B2 | 5/2003 | Thalgott |
| 6,562,074 B2 | 5/2003 | Gerbec et al. |
| 6,582,468 B1 | 6/2003 | Gauchet |
| 6,610,094 B2 | 8/2003 | Husson |
| 6,641,614 B1 | 11/2003 | Wagner et al. |
| 6,648,917 B2 | 11/2003 | Gerbec et al. |
| 6,676,665 B2 | 1/2004 | Foley et al. |
| 6,706,070 B1 | 3/2004 | Wagner et al. |
| 6,719,796 B2 | 4/2004 | Cohen et al. |
| 6,723,126 B1 | 4/2004 | Berry |
| 6,733,532 B1 | 5/2004 | Gauchet et al. |
| 6,743,255 B2 | 6/2004 | Ferree |
| 6,805,714 B2 | 10/2004 | Sutcliffe |
| 6,855,167 B2 | 2/2005 | Shimp |
| 6,863,673 B2 | 3/2005 | Gerbec et al. |
| 6,893,464 B2 | 5/2005 | Kiester |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 7,018,412 B2 | 3/2006 | Ferreira et al. |
| 7,018,416 B2 | 3/2006 | Hanson et al. |
| 7,037,339 B2 | 5/2006 | Houfburg et al. |
| 7,083,650 B2 | 8/2006 | Moskowitz et al. |
| 7,094,257 B2 | 8/2006 | Mujwid et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,326,248 B2 | 2/2008 | Michelson |
| 7,503,933 B2 | 3/2009 | Michelson |
| 7,507,241 B2 | 3/2009 | Levy et al. |
| 7,569,074 B2 | 8/2009 | Eiserman et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,691,147 B2 | 4/2010 | Gutlin et al. |
| 7,703,727 B2 | 4/2010 | Selness |
| 7,722,612 B2 | 5/2010 | Sala et al. |
| 7,722,674 B1 | 5/2010 | Grotz |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,819,921 B2 | 10/2010 | Grotz |
| 7,824,445 B2 | 11/2010 | Biro et al. |
| 7,837,734 B2 | 11/2010 | Zucherman et al. |
| 7,846,206 B2 | 12/2010 | Oglaza et al. |
| 7,850,733 B2 | 12/2010 | Baynham et al. |
| 7,854,766 B2 | 12/2010 | Moskowitz et al. |
| 7,874,980 B2 | 1/2011 | Sonnenschein et al. |
| 7,879,098 B1 | 2/2011 | Simmons, Jr. |
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,177,812 B2 | 5/2012 | Sankaran |

(56) References Cited

U.S. PATENT DOCUMENTS

| | | |
|---|---|---|
| 8,192,495 B2 | 6/2012 | Simpson et al. |
| 8,221,501 B2 | 7/2012 | Eiserman et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,095,446 B2 | 8/2015 | Landry et al. |
| 9,095,447 B2 | 8/2015 | Barreiro et al. |
| 9,101,488 B2 | 8/2015 | Malandain |
| 2002/0068976 A1 | 6/2002 | Jackson |
| 2002/0068977 A1 | 6/2002 | Jackson |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1* | 7/2007 | Hestad et al. ............ A61F 2/44 623/17.12 |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1* | 6/2008 | Reiley et al. ...... A61B 17/8855 606/192 |
| 2008/0140207 A1 | 6/2008 | Olmos |
| 2008/0147193 A1 | 6/2008 | Matthis et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |

(56) References Cited

U.S. PATENT DOCUMENTS

| | | |
|---|---|---|
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1* | 12/2011 | Palmatier et al. .... A61F 2/4455 623/17.16 |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2012/0197403 A1 | 8/2012 | Merves |
| 2012/0197405 A1 | 8/2012 | Cuevas et al. |
| 2012/0226357 A1 | 9/2012 | Varela |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0182347 A1 | 7/2015 | Robinson |

FOREIGN PATENT DOCUMENTS

| | | |
|---|---|---|
| DE | 202008001079 | 3/2008 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2874814 | 3/2006 |
| JP | 2003-526457 | 9/2003 |
| JP | 2006-516456 | 7/2006 |
| JP | 2011-509766 A | 3/2011 |
| WO | WO 95/31158 | 11/1995 |
| WO | WO 97/00054 | 1/1997 |
| WO | WO 00/12033 | 3/2000 |
| WO | WO 00/74605 | 12/2000 |
| WO | WO 01/01895 | 1/2001 |
| WO | WO 2005/112834 | 12/2005 |
| WO | WO 2006/047587 | 5/2006 |
| WO | WO 2006/058281 | 6/2006 |
| WO | WO 2006/065419 | 6/2006 |
| WO | WO 2006/081843 | 8/2006 |
| WO | WO 2007/009107 | 1/2007 |
| WO | WO 2007/028098 | 3/2007 |
| WO | WO 2007/048012 | 4/2007 |
| WO | WO 2008/044057 | 4/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 3/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |

(56) References Cited

FOREIGN PATENT DOCUMENTS

OTHER PUBLICATIONS

Krbec, [Replacement of the vertebral body with an expansion implant (Synex)], Acta Chir Orthop Traumatol Cech, 2002, pp. 158-162, vol. 69(3).
U.S. Appl. No. 61/675,975, filed Jul. 26, 2012, Lechmann et al.
International Patent Application No. PCT/US2013/029014: International Search Report dated Jul. 1, 2013, 7 pages.
Chiang, Biomechanical Comparison of Instrumented Posterior Lumbar Interbody Fusion with One or Two Cages by Finite Element Analysis, Spine, Sep. 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, Oct. 2003, pp. 455-460, vol. 16(5).
Hunt, Expanable cage placement via a posterolateral approach in lumbar spine reconstructions, Journal of Neurosurgery: Spine, Sep. 2006, pp. 271-274, vol. 5.
Polikeit, The importance of the endplate for interbody cages in the lumbar spine, Eur Spine J, Dec. 2003, pp. 556-561, vol. 12.
Shin, Posterior Lumbar Interbody Fusion via a Unilateral Approach, Yonsei Medical Journal, Jun. 2006, pp. 319-325, vol. 47(3).

\* cited by examiner

EXPANDABLE IMPLANT

CROSS REFERENCE TO RELATED APPLICATIONS

This application is a continuation of U.S. patent application Ser. No. 13/784,955, now allowed, which claims the benefit of and priority to U.S. Provisional Patent Application Ser. No. 61/675,975 filed Jul. 26, 2012, the contents of which are hereby incorporated by reference herein in their entirety.

TECHNICAL FIELD

This invention relates to improved implants for a skeletal space. This invention also relates to improved methods for expanding a skeletal space and for treating a patient having skeletal damage or injury.

BACKGROUND

There are many situations where there is a need to replace, augment or support sections of bone in human or animal bodies, such as for replacement of material between or within bones in the spine, long bones in the arms or legs, in the knee, hip, shoulder, finger or other joints and following removal of a portion of bone due to tumour treatment or injury. In particular, there is a requirement for support or realignment of neighbouring vertebrae for treating damage to the spine, for example due to osteoporosis or damage to a vertebral disc. Expandable intervertebral implants which can be inserted into a patient's spine at a relatively small size and which are able to expand to restore the original height of removed spinal material or to a height desired by a surgeon in order to support and/or realign the spine are known from WO 2009/092102.

WO 2009/092102 discloses implants that may be sequentially expanded in an intervertebral space using a surgical instrument to perform lateral expansion in the anterior-posterior (a-p) direction and then using a balloon to expand the implant in the cranio-caudal (c-c) direction. However, it has been found that when an instrument is used to expand the implant in the a-p direction, it is difficult to achieve the desired dimension of the intervertebral implant in the a-p direction (the implant "footprint"). One reason for this is the difficulty in accessing the implant with an appropriate instrument when the implant is located in a surgically sensitive site, such as between vertebrae, due to the potential risk of tissue and nerve damage to the patient. An alternative method for effecting a-p expansion of the implant disclosed in WO 2009/092102 is using the pre-installed balloon. However, this results in an inherent expansion of the implant in the c-c direction. A disadvantage of this arrangement is that there is a risk that the implant will contact the vertebrae too early during the c-c expansion, thereby limiting the a-p expansion achievable and, hence, preventing the degree of a-p expansion within the intervertebral space desired by the surgeon. A consequence of insufficient a-p expansion of the implant is that the implant may be less effective at supporting and/or aligning the vertebrae and may not allow sufficiently high biomechanical performance.

It is desirable to provide an expandable implant that is able to be inserted into a skeletal space in a patient at a relatively small size and which is configured to be able to expand in a controlled, sequential fashion to dimensions desired by a medical practitioner. In particular, it is desirable to be able to restrict expansion in at least one direction in which the implant is able to expand during expansion of the implant in a perpendicular direction, in order to provide more control over the dimensions of the finally expanded implant.

Furthermore, it would be desirable to provide a method of expanding a skeletal space using an expandable implant in a sequential fashion that allows the dimensions of the expanded implant to be controlled.

SUMMARY

According to the present invention, there is provided an implant for a skeletal space, comprising:
 a first contacting member;
 a second contacting member;
 at least one first expansion compartment; and
 at least one second expansion compartment;
 wherein the implant is expandable from an insertion configuration to an expanded configuration,
 wherein the implant has a first dimension in a first direction and a second dimension in a second direction in the insertion configuration, and wherein the first direction is substantially perpendicular to the second direction,
 wherein the implant is configured such that:
  during expansion of the at least one first expansion compartment, the at least one first expansion compartment cooperates with at least one of the first and second contacting members to cause the first dimension of the implant to increase without substantially causing a change in the second dimension of the implant; and
  during expansion of the at least one second expansion compartment, the at least one second expansion compartment cooperates with at least one of the first and second contacting members to cause the second dimension of the implant to increase.

As such, the implant can be expanded in the first direction to achieve the required first dimension for the implant within a skeletal space without changing the second dimension of the implant and then subsequently can be expanded in the second direction to achieve the required second dimension of the implant within the skeletal space. An advantage of the implant is that it allows expansion in at least one dimension of the implant to be restricted during expansion of the implant in another dimension. Having the ability to select the direction in which the dimension of the implant is able to expand, provides a medical practitioner with improved control over expanding the implant to the appropriate dimensions within the skeletal space.

The implant may be configured such that during expansion of the at least one second expansion compartment, the at least one second expansion compartment cooperates with at least one of the first and second contacting members to cause the second dimension of the implant to increase without substantially causing a change in the first dimension of the implant. As such, the implant can be expanded in the first direction to achieve the required first dimension for the implant within a skeletal space without changing the second dimension of the implant and then subsequently can be expanded in the second direction to achieve the required second dimension of the implant within the skeletal space without affecting the previously obtained first dimension. Alternatively, the implant may be expanded initially in the second direction with subsequent expansion in the first direction. In this way, the implant provided has an advantage of being able to be expanded in a controlled fashion so that both first and second dimensions of the implant may be optimised.

The implant may be manufactured by any appropriate means. For example, the implant may be manufactured by manufacturing each of the first and second contacting members as separate and distinct components and then coupling these together. An exemplary method for making the implants of the present invention may be based on the method described in WO 2009/092102, or any appropriate adaptation thereof known to a person skilled in the art.

The implant may be used in any appropriate skeletal space. The implant of the present invention may be used for replacement of material between or within bones, such as in the spine, long bones in the arms or legs, in the knee, hip, shoulder, finger or other joints. Alternatively, the implant of the present invention may be used for replacement of a section of bone, such as following removal of a portion of bone due to tumour treatment or injury. The skeletal space may correspond to a section of bone removed from a femur, tibia or fibula. The skeletal space may be defined by a void between a first portion and a second portion of the same bone. Alternatively, the skeletal space may be defined by a void between a first bone and a second bone. Preferably, the skeletal space is a void between a first bone and a second bone in a joint. Preferably, the skeletal space is an intervertebral space. The intervertebral space may arise from the absence of an intervertebral disc. The intervertebral space may be defined by the space between the superior surface of a first vertebra and an inferior surface of a second, adjacent vertebra.

The first direction and second direction are substantially perpendicular to each other. The first direction and second direction may be in any direction depending on the orientation of the implant. The first direction may correspond to the direction of the height, width or depth of the implant. The second direction may correspond to the direction of the height, width or depth of the implant. Preferably, the first direction corresponds to the width of the implant and the second direction corresponds to the height of the implant. In this arrangement, the extent of the expansion of the implant in the first direction may be selected according to the width of a skeletal space and the extent of the expansion of the implant in the second direction may be selected according to the distance between a first bone or first portion of bone and a second bone or second portion of bone defining the skeletal space. Where the skeletal space is an intervertebral space, the first direction may be an anterior-posterior (a-p) direction, a cranio-caudal (c-c) direction or a medial laterally (m-l) direction. Preferably, the first direction is an a-p direction and the second direction is a c-c direction.

The first and the second contacting members may be bone contacting members. The portion of bone which the first and second contacting members contact may be bare bone or may be covered in a material, such as a protective cap or a film layer to assist in engagement of the bone with the implant.

The first and the second contacting members may be substantially planar. Alternatively, they may be shaped, such as having a convex or a concave shaped in order to better align with the portion of the bone which they abut.

The first and second contacting members may have an outer surface that contacts bone which is smooth.

Alternatively, the outer surface of the first and second contacting members may have an outer surface that is undulating. The outer surface may comprise a plurality of teeth or spikes. In this way the implant may have improved stability within the skeletal space. In particular, there may be improved engagement between the implant and the bone due to friction between the bone and the plurality of teeth.

The first and second contacting members may be formed from any suitable biocompatible material including: a metal, such as cobalt-chromium-molybdenum (CCM) alloys, titanium, titanium alloys, stainless steel, aluminium; a ceramic such as zirconium oxide, silicone nitride; an allograft; an autograft; a metal-allograft composite; a polymer, such as polyaryl ether ketone (PAEK), polyether ether ketone (PEEK), polyether ketone ketone (PEKK), polyetherketone (PEK), polyetherketone ether-ketone-ketone (PEK-EKK); and polymers reinforced with a fiber, such as a carbon fiber.

The first and second contacting members may be coated in order to enhance the osteo-integration of the implant in the skeletal space. The first and second contacting members may also be coated with thin layer titanium using a physical or chemical vapour deposition process, by an anodic plasma chemical surface treatment comprising calcium and/or phosphorus in the titanium-oxide surface layer or may be sprayed with a titanium or hydroxyapatite (HA) plasma. In this way osteo-conductive properties may be enhanced.

The first and second expansion compartments may be an inflatable structure, such as a balloon, an expansion sack or an expansion bag. Preferably, the first expansion compartment is a balloon, preferably a double-walled balloon. Preferably, the second expansion compartment is a balloon, preferably a double-walled balloon. Preferably, the first and second expansion components are both balloons, preferably double-walled balloons.

The first and second expansion compartments may be manufactured from any suitable biocompatible material including, polyurethane, a polycarbonate urethane, a polycarbonate-silicone urethane copolymer, a polyamine, a polyethylene terephthalate, and a polycaprolactone.

The use of expansion compartments in the implant enables selective, sequential expansion of the implant. Furthermore, the expansion compartments allow the implant filling material to be safely retained in order to avoid the filling material spreading out of the implant and into sensitive and easily damaged body parts.

The implant may comprise a single first expansion compartment, two first expansion compartments, or more than two first expansion compartments. Preferably, the implant comprises two first expansion compartments.

The implant may comprise a single second expansion compartment, two second expansion compartments, or more than two second expansion compartments. Preferably, the implant comprises two second expansion compartments.

The first and second expansion compartments may be configured to be able to receive a filling material independently of one another. In this way, expansion of the first and second expansion compartments can occur selectively, which has an advantage of allowing improved control over the manner in which the implant expands.

Typically, the first and second expansion compartments may each be connected to separate removable catheters. Filling material may be introduced into the expansion compartment via a catheter. The first and second expansion compartments may each comprise an entry portion into which the filling material may be introduced. Once a required amount of filling material has been introduced into the expansion compartment, the catheter may be removed.

The filling material may be any suitable biocompatible material and may be rigid or elastic. The filling material may be a bone cement, a hydrogel, a polyvinyl alcohol, a sodium polyacrylate, an acrylate polymer, a methyl-methacrylate, a copolymer with an abundance of hydrophilic groups, p-vinyl pyrollidone, polyethyleneimine, a setting or curing hydrogel based copolymer such as polyethyleneimine, poly(diethylaminoethyl methacrylate), poly(ethylaminoethyl methacrylate), a thermally setting hydrogel based copolymer such as poly-N-isopropylacrylamide with polyethylene glycol, copolymers of polyethylene oxide and polyphenelylene oxide, copolymers of polyethylene glycol and polyactides, an ionic setting hydrogel such as ethylacrylate, methacrylic acid, 1,4-butanediacrylate, or a PCU, PCU-silicone copolymer, silicone or other non-resorbable pure or elastic copolymer (for example, PCU's silicone end group modified PUs, RTV curing siloxane based elastomers).

The filling material may be curable, for example, the filling material may comprise a polymer and a cross-linking agent. The final dimensions and shape of the implant after expansion may be retained by hardening or cross-linking the filling material after the filling material has been introduced into the expansion compartment. In this way, the implant may be able to provide skeletal support where previously there had been a space.

The implant may comprise a first cavity defined in a region between the first contacting member and the second contacting member in which at least one of the second expansion compartments is housed.

The implant may further comprise a second cavity defined in a region between the first contacting member and the second contacting member in which a further second expansion compartment is housed.

The first contacting member may comprise two contacting components. Where the first contacting member comprises two contacting components, the implant further comprises a first expandable connection that links the two contacting components. The two contacting components of the first contacting member are arranged such that as the first dimension of the implant increases the first expandable connection expands and the contacting components move apart.

A third cavity may be defined in a region between the two contacting components of the first contacting member in which a first expansion compartment is housed. In this way, expansion of the first expansion compartment moves apart the two contacting components of the first contacting member.

The second contacting member may comprise two contacting components. Where the second contacting member comprises two contacting components, the implant further comprises a second expandable connection that links the two contacting components. The two contacting components of the second contacting member are arranged such that as the first dimension of the implant increases the first expandable connection expands and the contacting components move apart.

A fourth cavity may be defined in a region between the two contacting components of the second contacting member in which a first expansion compartment is housed. In this way, expansion of the first expansion compartment moves apart the two contacting components of the first contacting member.

The implant may comprise a third expandable connection that links the first contacting member to the second contacting member, wherein as the second dimension of the implant increases the third expandable connection expands.

The first, second or third expandable connections may comprise any elements that allow the contacting components or contacting members to which they are linked to move apart as described hereinabove. The expandable connections may comprise, for example, a mesh or a wire netting. The wire netting may comprise a plurality of individual link members. The individual link members may have a rectangular shape. The individual link members may have a trapezoidal shape.

The first and/or second expandable connections may comprise the at least one first expansion compartment described hereinabove. A first expansion compartment may be attached to each of the two components of one or both of the first and second contacting members such that on expansion of the first expansion compartment, the two components of the first or the second contacting members are moved apart by and remain linked together by the first expansion component. The third expandable connection may comprise the at least one second expansion compartment described hereinabove. A second expansion compartment may be attached to each of the first and second contacting members such that on expansion of the second expansion compartment, the first and second contacting members are moved apart by and remain linked together by the second expansion component.

The first, second and third expandable connections may allow expansion of the implant to any suitable dimension appropriate for the skeletal space in which the implant is being used. When the skeletal space is an intervertebral space, the expandable connections typically are each able to expand from about 0.3 mm to about 12 mm.

The first, second and third expandable connections may allow the first and second contacting members to adopt a shape that enables the implant to adapt to the shape of the skeletal space.

The implant may further comprise at least one third expansion compartment,
wherein the implant has a third dimension in a third direction in the insertion configuration, and the third direction is substantially perpendicular to each of the first and second directions,
wherein the implant is configured such that expansion of the at least one third expansion compartment causes the third dimension of the implant to increase without substantially causing a change in the first or second dimensions of the implant.

At least one, preferably both, of the first and second contacting members may each comprise four contacting components. The four contacting components may be arranged in a configuration such that there are two contacting components side by side in the first direction and two contacting components side by side in the third direction. The at least one third expansion compartment may be positioned between two contacting components in the third direction. Expansion of the third expansion compartment is able to move apart the two contacting components in the third direction. Preferably, the third expansion compartment is as hereinbefore described in relation to the first and second expansion compartments.

Where the first and second directions are height and width of the implant, the third direction corresponds to the depth of the implant. Preferably, where the skeletal space is an intervertebral space, the third direction is the m-l direction.

The implant may further comprise a first fixing for attaching the at least one first expansion compartment to the implant. The first expansion compartment may comprise an attachment portion, such as a hook portion, for cooperating with the first fixing and allowing attachment to the implant.

The implant may further comprise a second fixing for attaching the at least one second expansion compartment to the implant. The second expansion compartment may comprise an attachment portion, such as a hook portion, for cooperating with the second fixing and allowing attachment to the implant.

The first and second fixings may be arranged at an end of the implant away from the end at which the entry portion of the first and second expansion compartments is located.

The first and second fixings may be configured to allow detachment from the implant of the at least one first expansion compartment and the at least one second expansion compartment when the implant is in the expanded configuration. In this way, the position of the first or second expansion compartments may be manipulated to allow tilting of the first contacting member of the implant with respect to the second contacting member. In an embodiment where the first and/or second contacting members comprise two or more contacting components, relative movement of one or more contacting components within a plane of the first and/or second contacting members may be achieved.

Detachment of the first or second expansion compartment from the implant may also be advantageous in the event that the implant should be removed from the skeletal space. Removal of the first or second expansion compartments may allow the implant to reduce in size and adopt the insertion configuration, which would make removal from the skeletal space less damaging to the patients other body parts.

The implant may comprise a mechanism for engaging an implant holding and/or insertion instrument. The mechanism for engaging an implant holding and/or insertion instrument may comprise one or more grooves, apertures, mouldings, channels or projections arranged on the first or second contacting members. For example, the mechanism may be arranged to receive one or more pairs of blade springs of an implant holding and/or insertion instrument.

The implant may comprise one or more features, such as one or more form fit features, that assist the contacting components of the first and second contacting members to fit together prior to expansion of the first and/or second expansion compartments. These features are useful in order to help retain the implant in an insertion configuration during implantation. These features may comprise one or more grooves, apertures, mouldings, channels or projections arranged on the first or second contacting members to enable the first and second contacting members to retain their position relative to each other prior to expansion of the implant.

In accordance with the present invention, there is provided a method of expanding an implant in a skeletal space comprising:

inserting an expandable implant in a skeletal space, the implant comprising first and second expansion compartments;

expanding the first expansion compartment to expand a first dimension of the implant in a first direction; and subsequently expanding the second expansion compartment to expand a second dimension of the implant in a second direction;

wherein the first direction is different to the second direction.

The first direction may be perpendicular to the second direction.

The method may comprise a step of arranging the first and second expansion compartments in the expandable implant prior to inserting the expandable implant in a skeletal space. Alternatively, the method may comprise a step of providing an implant in which the first and second expansion compartments have been arranged in the implant prior to insertion of the implant.

The method may comprise preventing substantially any expansion of the second dimension of the implant in a second direction during the step of expanding the first expansion compartment. Alternatively or in addition, the method may comprise preventing substantially any expansion of the first dimension of the implant in a first direction during the step of expanding the second expansion compartment.

The method may further comprise evaluating the position of the implant prior to expanding the second expansion compartment. Evaluation of the position of the implant may be achieved by using standard techniques such as fluoroscopy. A fluoroscope, also known as an image intensifier, may be used to evaluate the position of the implant intraoperatively and in real time. The implant may be engaged with an implant holding and/or insertion instrument during the evaluation. This has an advantage of allowing repositioning of the implant as appropriate.

Prior to insertion of the implant, the end portions of the bone at the edge of the skeletal plates may be cleaned. Furthermore, tissue may be removed from the skeletal space prior to insertion of the implant.

The skeletal space is as hereinbefore described. Preferably, the skeletal space is an intervertebral space. Where the skeletal space is an intervertebral space, the method preferably comprises a step of removing an intervertebral disc from the intervertebral space prior to the step of inserting the implant in the intervertebral space.

The implant may be inserted in an intervertebral space via abdominal, trans-psoas or extraforaminal approaches.

The implant used in the method of the present invention may have features as in any of the implants hereinbefore described.

The implant may comprise a first contacting member and a second contacting member. Preferably, the first and the second contacting members are bone contacting members. The implant may be configured such that in the step of expanding the first expansion compartment, the first expansion compartment cooperates with at least one of the first and second contacting members to cause the first dimension of the implant to increase. Alternatively or in addition, the implant may be configured such that in the step of expanding the second expansion compartment, the second expansion compartment cooperates with at least one of the first and second contacting members to cause the second dimension of the implant to increase.

In the method of the present invention, the implant may have at least two second expansion compartments, and the method may comprise expanding one second expansion compartment more than the other second expansion compartment in order to tilt the first contacting member with respect to the second contacting member.

According to the present invention there is provided a method of treating skeletal damage in a patient comprising implanting in a skeletal space an implant of the present invention.

According to the present invention there is provided a method of treating skeletal damage in a patient comprising inserting an implant of the present invention and expanding the implant according to the method of expanding a skeletal space hereinbefore described.

DETAILED DESCRIPTION

Specific embodiments of the present invention are now described by way of example only with reference to the drawings. It will be recognised that features specified in one embodiment of the invention may be combined with other specified features to provide further embodiments.

Figure 1:
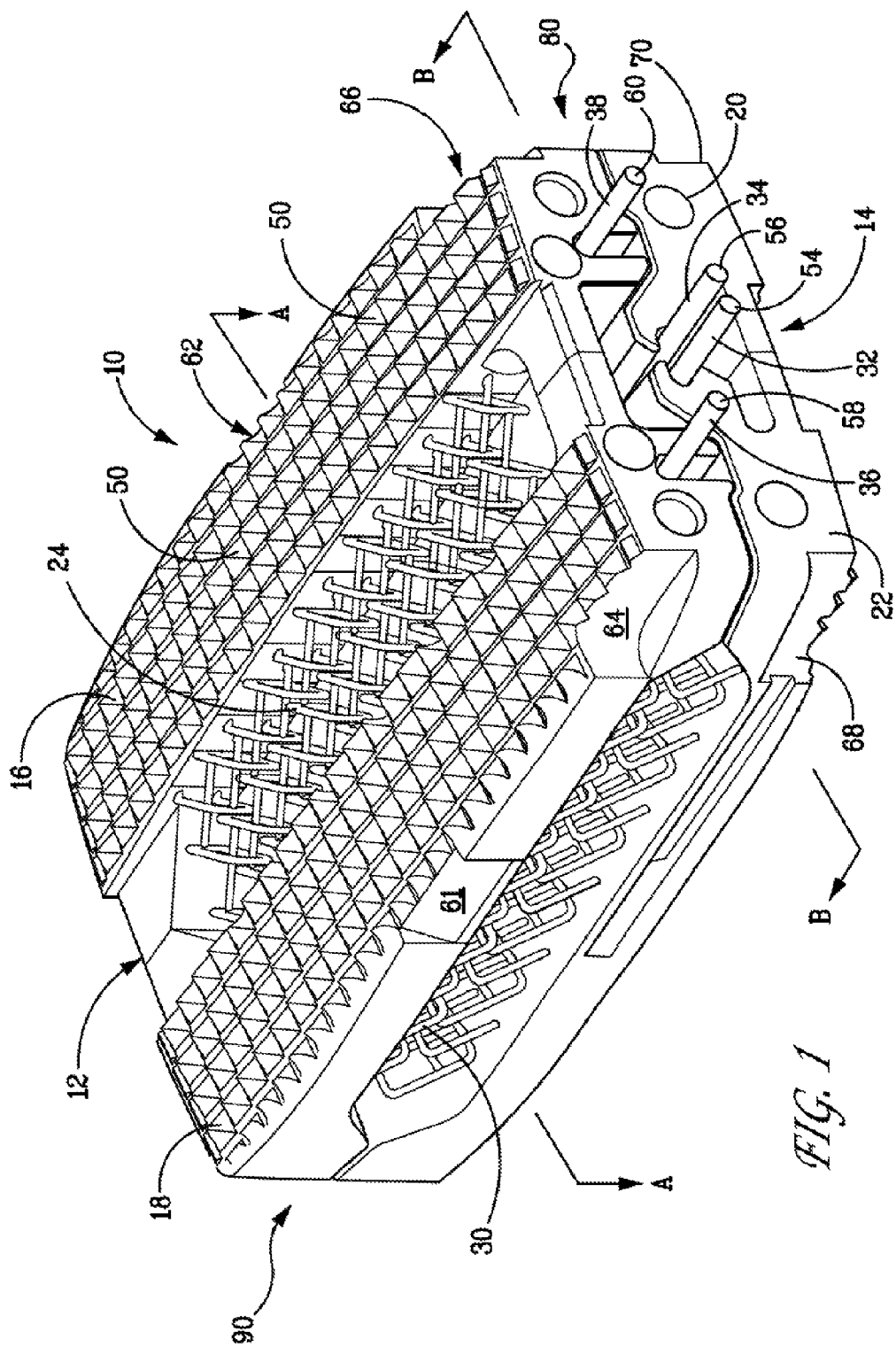
FIG. 1 is a top perspective view of an implant according to the present invention in an insertion configuration.
Figure 2:
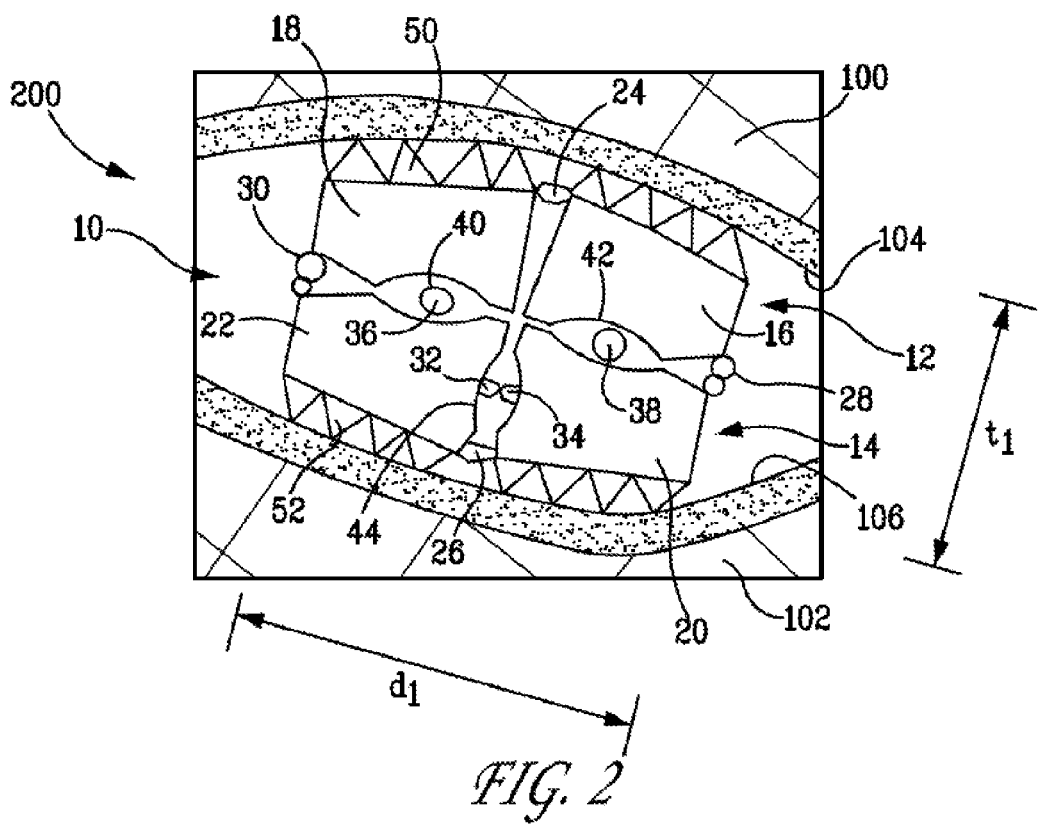
FIG. 2 is a cross-sectional view of the implant shown in FIG. 1 taken through the plane A-A.
Figure 3:
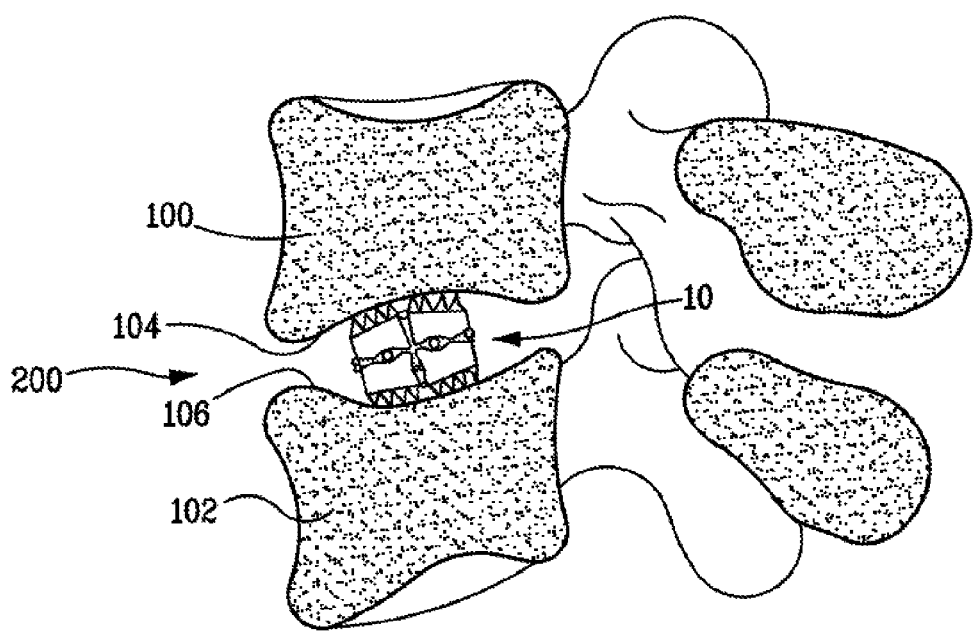
FIG. 3 is a cross-sectional view of an implant shown in FIG. 1 positioned in an intervertebral space.

With reference to FIGS. 1, 2 and 3, an implant (10) according to one embodiment of the present invention is shown in an insertion configuration. The implant has a front end (80) and a rear end (90). The implant (10) has a first contacting member (12) consisting of two contacting components (16, 18) linked by a first expandable connection (24) and a second contacting member (14) consisting of two contacting components (20, 22) linked by a second expandable connection (26). The first contacting member (12) and the second contacting member (14) are linked by a third expandable connection (28, 30).

The implant (10) has a first cavity (40) between one contacting component (18) of the first contacting member (10) and one contacting component (22) of the second contacting member (14) in which is housed a second expansion compartment (36). The implant (10) also has a second cavity (42) between the other contacting component (16) of the first contacting member (12) and the other contacting component (20) of the second contacting member (14) in which is housed a further second expansion compartment (38). The two second expansion compartments are in the form of longitudinally shaped balloons.

The implant (10) has a third cavity (44) between the contacting components (20, 22) of the second contacting member (14) in which are housed two first expansion compartments (32, 34). The first expansion compartments are in the form of longitudinally shaped balloons.

The contacting components (16, 18) of the first contacting member (12) each have a plurality of teeth (50) on their outermost surface. The contacting components (20, 22) of the second contacting member (14) each have a plurality of teeth (52) on their outermost surface.

The two first expansion compartments (32, 34) may be filled with filling material via a catheter (not shown) attached to an entry portion (54, 56) of each of the first expansion compartments.

The two second expansion compartments (36, 38) may be filled with filling material via a catheter (not shown) attached to an entry portion (58, 60) of each of the second expansion compartments.

The first contacting member (12) comprises a groove (61, 62) on the outer edge of each of the contacting components (16, 18) to which an implant holding and insertion instrument (not shown) can be attached to the implant (10).

The first contacting member (12) comprises recesses (64, 66) and the second contacting member comprises recesses (68, 70) to which an implant holding and insertion instrument (not shown) can be attached to the implant (10).

While in the insertion configuration, the implant (10) may be inserted into a skeletal space. FIGS. 2 and 3 show the implant (10) inserted into an intervertebral space (200) between a first vertebra (100) and a second vertebra (102). The implant (10) may be inserted into the intervertebral space (200) through a lateral incision in a patient. An implant holding and insertion instrument (not shown) engages with an arrangement of grooves (61, 62) and recesses (64, 66, 68, 70) on the implant (10) and the implant holding and insertion instrument is used to insert the implant into the intervertebral space (200). The implant holding and insertion instrument (not shown) is then detached from the implant (10). In the insertion configuration, the implant has a dimension $d_1$ in a first direction and a dimension $t_1$ in a second direction.

When inserted into the intervertebral space, the plurality of teeth (50) on the outermost surface of the first contacting member (12) engage with a surface (104) of the first vertebra (100) and the plurality of teeth (52) on the outermost surface of the second contacting member (14) engage with a surface (106) of the second vertebra (102).

Figure 4:
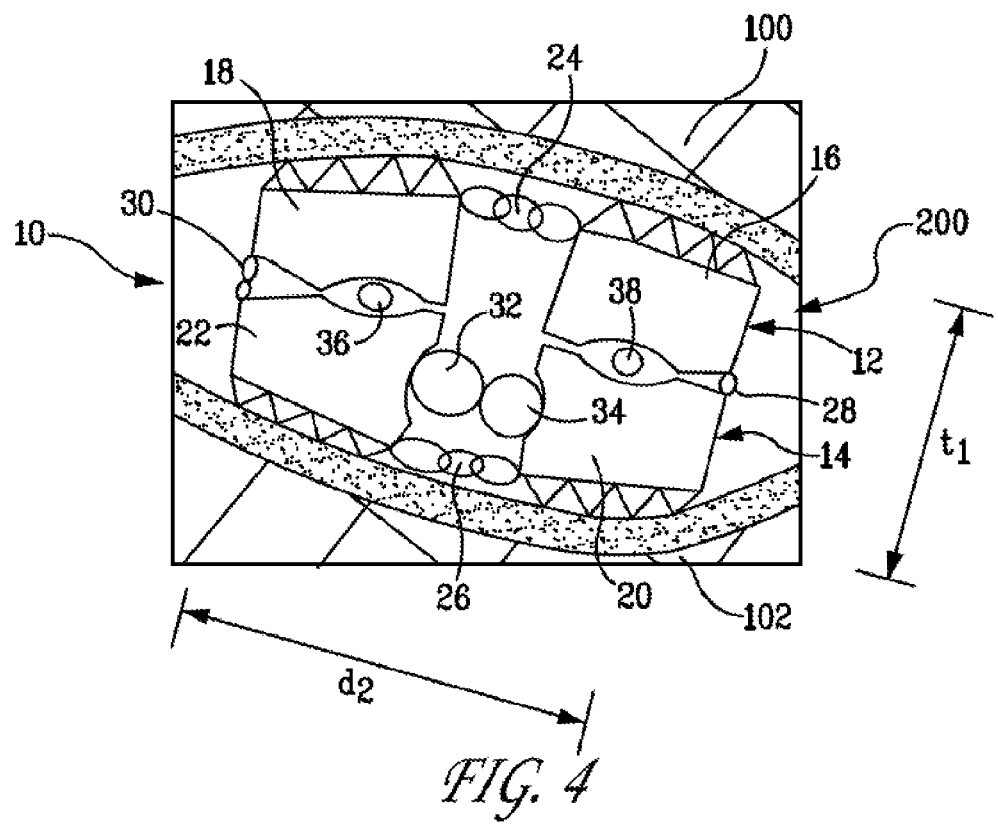
FIG. 4 is a cross-sectional view of the implant shown in FIG. 1 which has been expanded in a first direction.
Figure 5:
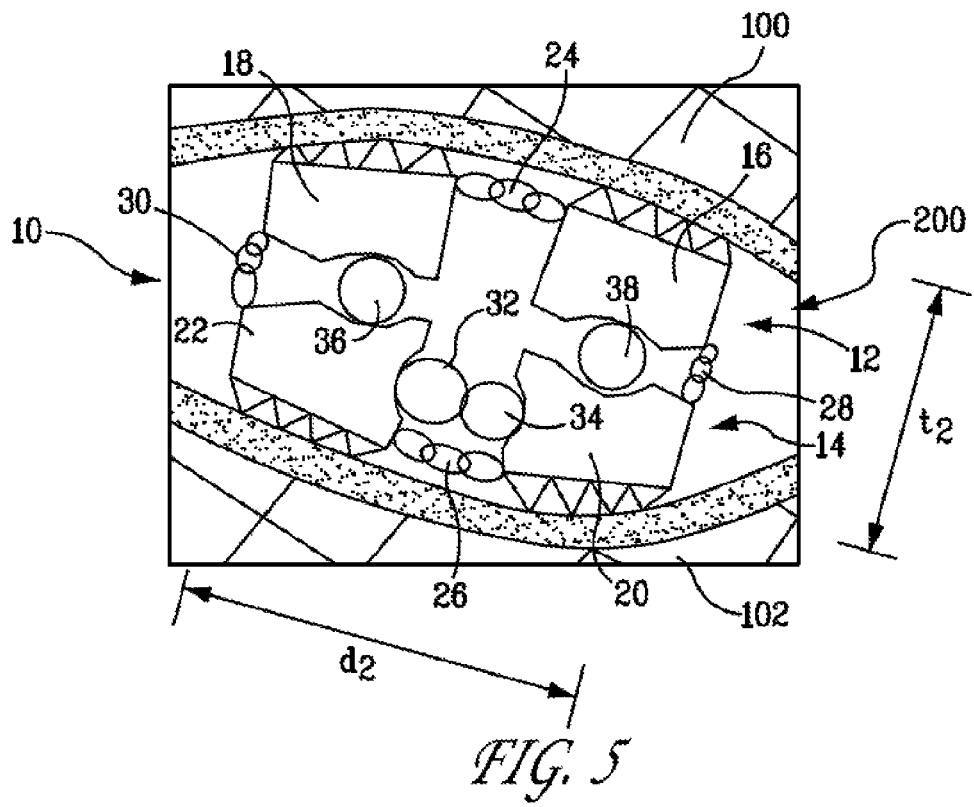
FIG. 5 is a cross-sectional view of the implant shown in FIG. 1 which has been expanded in a first direction and in a second direction.

With reference to FIGS. 4 and 5, which show features corresponding to those in FIGS. 2 and 3, the sequential expansion of the embodiment described in FIGS. 1 to 3, is effected by first simultaneously expanding the first expansion compartments (32, 34) with a filler material via catheters (not shown). Expansion of the first expansion compartments (32, 34) causes the first expandable connection (24) and the second expandable connection (26) to expand and the contacting components (16, 18) in the first contacting member (12) to move apart such that the implant has a dimension $d_2$ in the first direction. The third expandable connection (28, 30) does not expand and the dimension $t_1$ in the second direction remains unchanged. In this embodiment, the implant (10) is inserted such that the first direction corresponds to the a-p direction.

Subsequent to expansion of the first expansion compartments (32, 34), expansion in second direction, which corresponds to the c-c direction, is effected by simultaneously expanding the second expansion compartments (36, 38). Expansion of the second expansion compartments (36, 38) causes the third expandable connection (28, 30) to expand and the first and second contacting members (12, 14) to move apart such that the implant has a dimension $t_2$ in the second direction. The dimension $d_2$ in the second direction remains unchanged.

Figure 6:
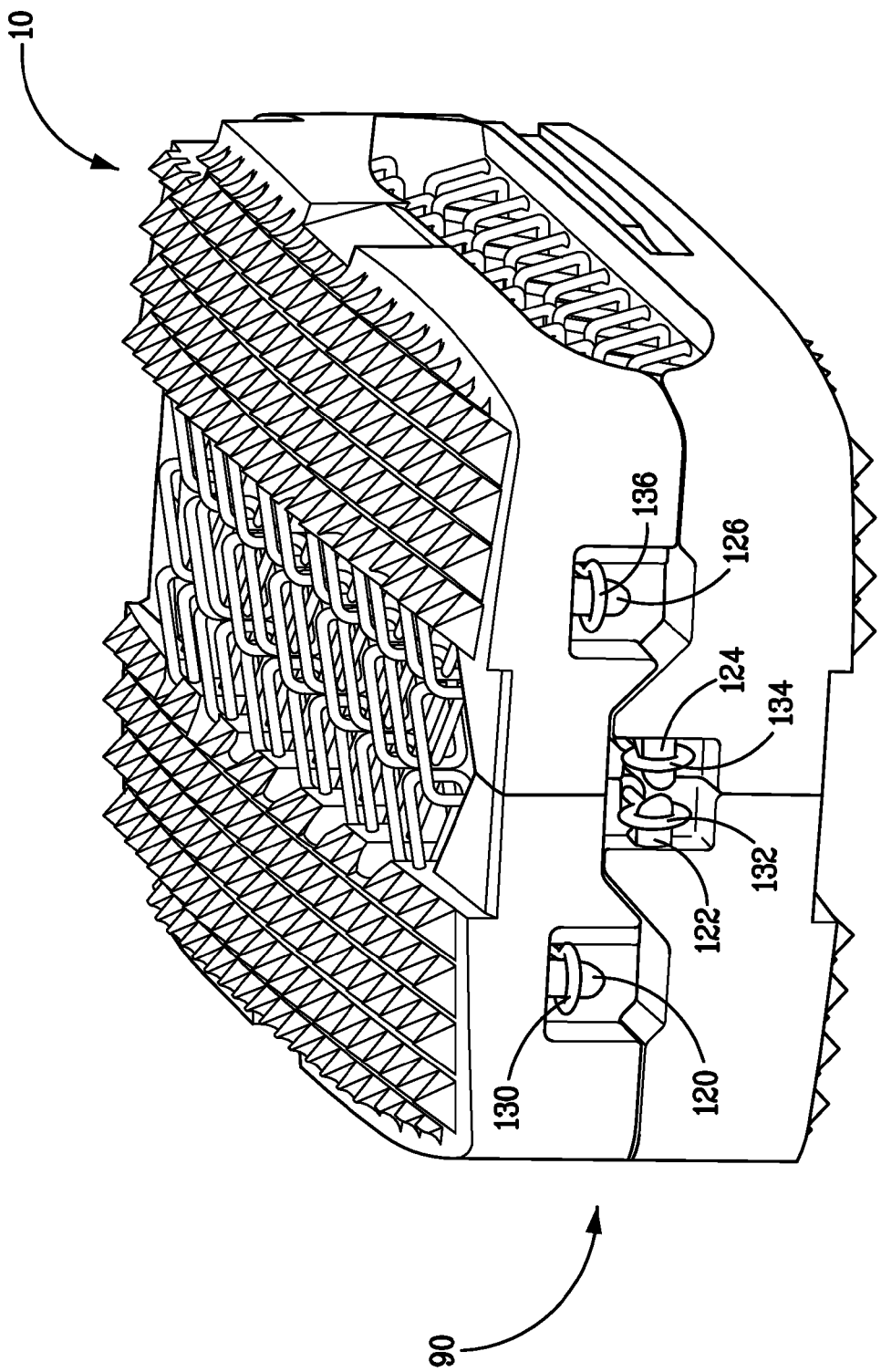
FIG. 6 is a rear perspective view of the implant shown in FIG. 1 in an insertion configuration.
Figure 7:
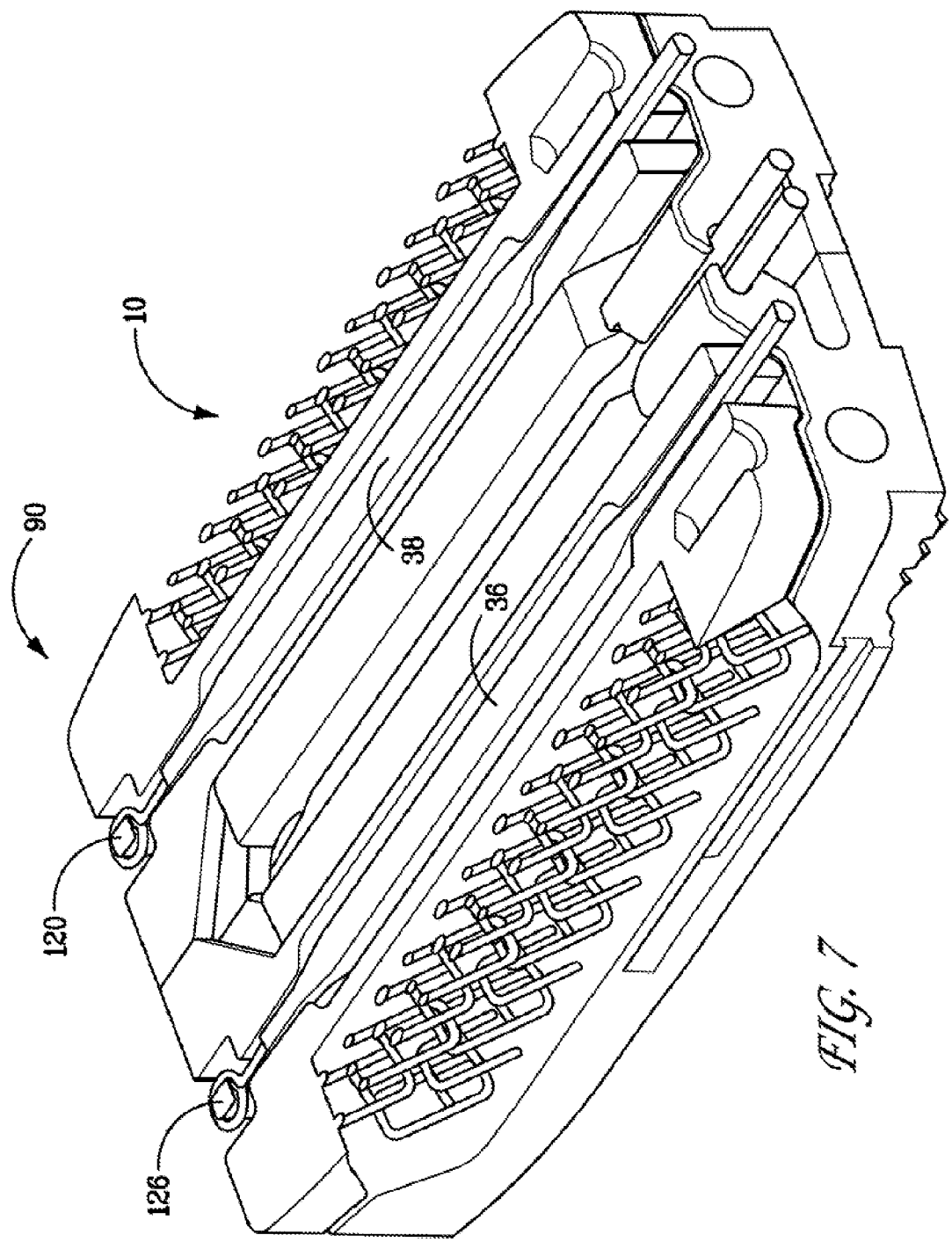
FIG. 7 is a cross-sectional view of the implant shown in FIG. 1 taken through the plane B-B.

With reference to FIGS. 6 and 7 the first expansion compartments (32, 34) each comprise a hook portion (132, 134) that cooperates with first fixings (122, 124) positioned at the rear end (90) of the implant (10) to attach the first expansion compartments (32, 34) to the implant (10). The second expansion compartments (36, 38) each comprise a hook portion (130, 136) that cooperates with second fixings (120, 126) positioned at the rear end (90) of the implant (10) to attach the second expansion compartments (36, 38) to the implant (10).

Figure 8:
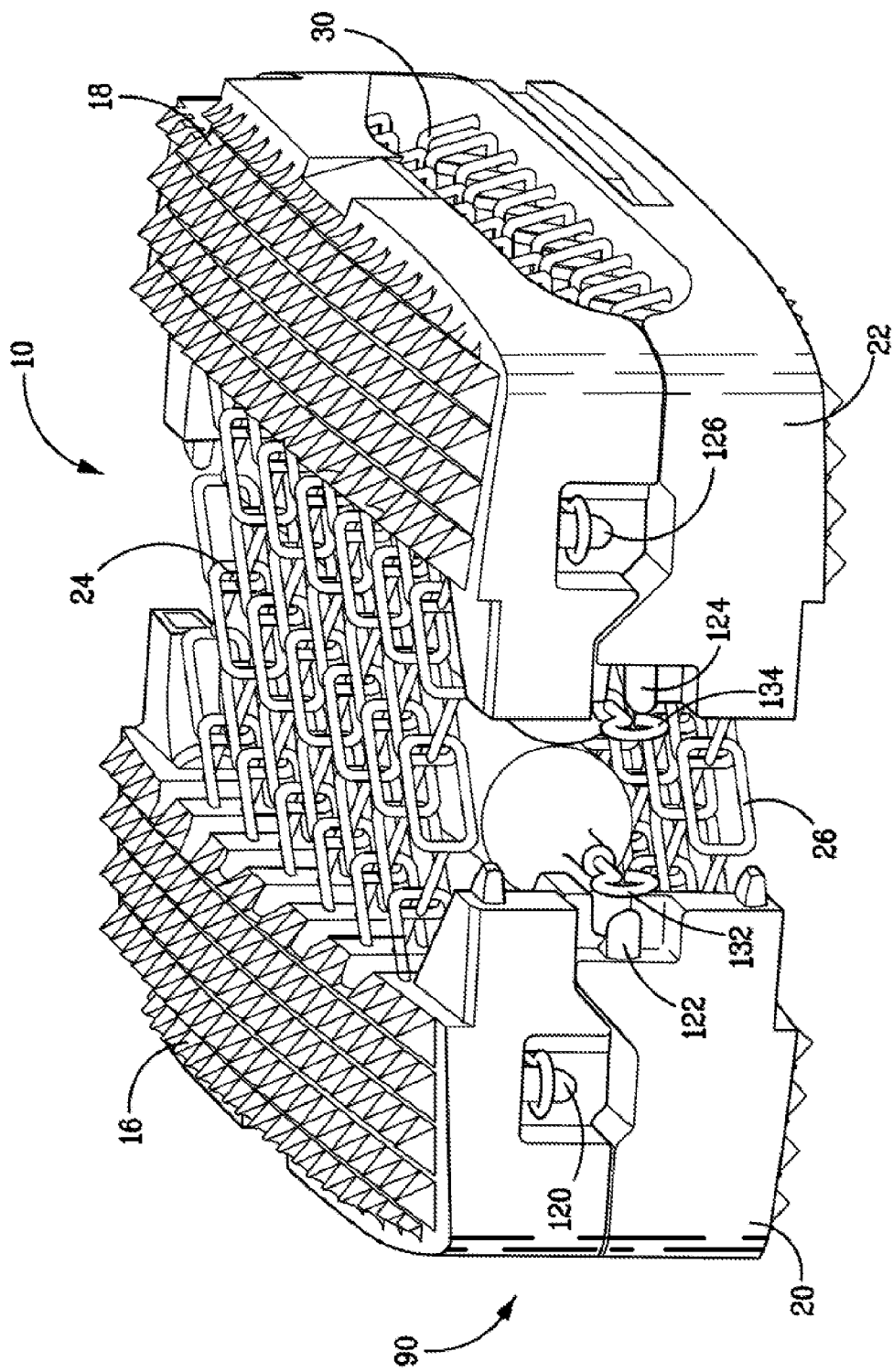
FIG. 8 is a rear perspective view of the implant shown in FIG. 1 which has been expanded in a first direction.
Figure 9:
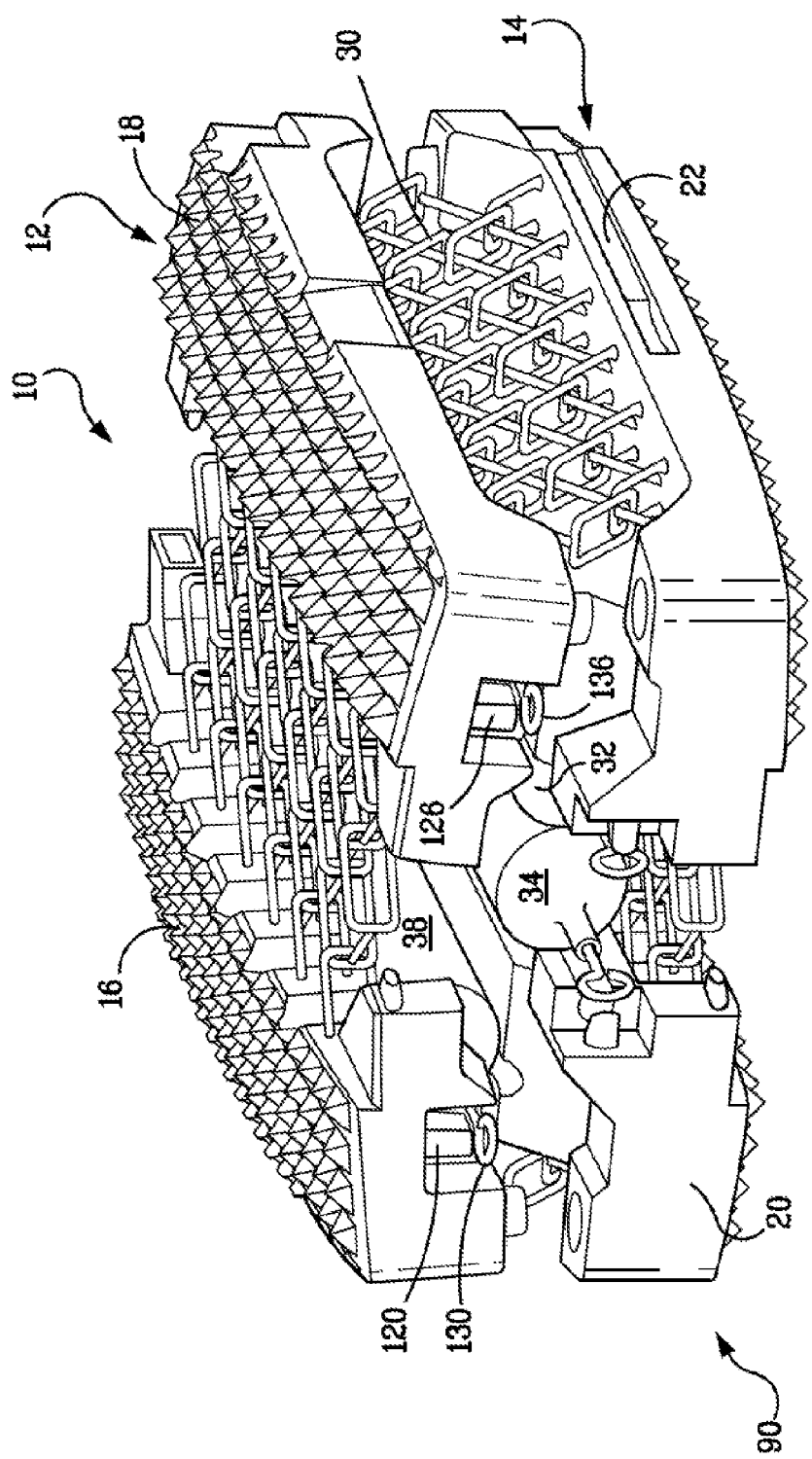
FIG. 9 is a rear perspective view of the implant shown in FIG. 1 which has been expanded in a first direction and in a second direction.

With reference to FIGS. 8 and 9, as the first expansion compartments (32, 34) expand, the contacting components (16, 18) of the first contacting member move apart, the contacting components (20, 22) of the second contacting member move apart and the first and second expandable connections (24, 26) expand. This expansion allows the hook portions (132, 134) of first expansion compartments (32, 34) to slide off the first fixings (122, 124) and hence the first expansion compartments (32, 34) detach from the implant (10).

As the second expansion compartments (36, 38) expand, the contacting components (16, 18) of the first contacting member move apart from the contacting components (20, 22) of the second contacting member and the third expandable connection (30) expands. This expansion allows the hook portions (130, 136) of the second expansion compartments (36, 38) to slide off the second fixings (120, 126) and hence the second expansion compartments (36, 38) detach from the implant (10).

With reference to FIG. 9, following detachment of the first and second expansion compartments (32, 34, 36, 38), the contacting components (16, 18) of the first contacting member (12) are able to tilt relative to each other and relative to the respective contacting components (20, 22) of the second contacting member (14).

Figure 10:
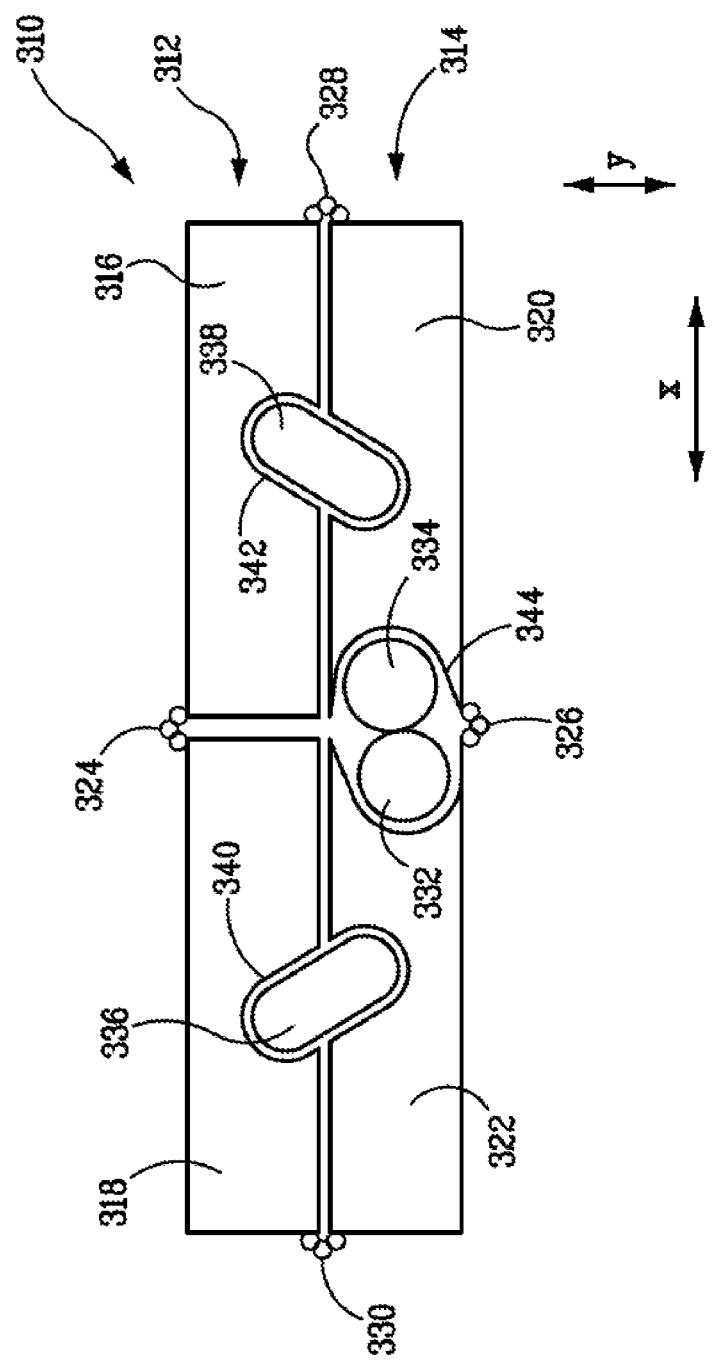
FIG. 10 is a cross-section view of an alternative implant according to the present invention in an insertion configuration.

With reference to FIG. 10, an implant (310) according to an alternative embodiment of the present invention is shown in an insertion configuration. The implant (310) has a first contacting member (312) consisting of two contacting components (316, 318) linked by a first expandable connection (324) and a second contacting member (314) consisting of two contacting components (320, 322) linked by a second expandable connection (326). The first contacting member (312) and the second contacting member (314) are linked by a third expandable connection (328, 330).

The implant (310) has a first cavity (340) between one contacting component (318) of the first contacting member (310) and one contacting component (322) of the second contacting member (314) in which is housed a second expansion compartment (336). The implant (310) also has a second cavity (342) between the other contacting component (316) of the first contacting member (310) and the other contacting component (320) of the second contacting member (314) in which is housed a further second expansion compartment (338).

The implant (310) has a third cavity (344) between the contacting components (320, 322) of the second contacting member (314) in which are housed two first expansion compartments (332, 334).

Expansion of the first expansion compartments (332, 334) causes the contacting components (320, 322) of the second contacting member (314) to move apart and the first and second expandable connections (324, 326) to expand. In this way, the implant (310) increases in dimension in a first direction (x). Due to the angled shape of the cavities (340, 342) between the first and second expansion members (312,314), expansion of the second expansion compartments (336, 338) causes the first contacting member (312) to move apart from the second contacting member (314), causing the third expandable connection (328, 330) to expand and, in addition, causes contacting components (316, 318) of the first contacting member (312) to move further apart and the first expandable connection (324) to further expand.

EXAMPLES

Embodiments of the present invention are now described, by way of illustration only, in the following examples. It will be understood that these examples are not limiting and that variations and modifications may be made within the spirit and scope of the invention as set out above and as defined in the following claims.

Example 1

Four separate catheter balloons (OPN NC® High Pressure PTCA Balloons from Sis Medical, having a highest rated burst pressure of 35 bar) were inserted into a bottom end of a cannulated implant holding and insertion instrument and pushed through the instrument such that part of the tubes connected to the catheter balloons were retained within the instrument but catheter balloons protruded from the top end of the instrument. The four balloons were subsequently inserted into an implant as shown in FIG. 1. The implant was mounted on the implant holding and insertion instrument using a pair of protruding blade springs which engaged with grooves on either side of the implant and retained the implant in a compressed, insertion configuration.

A lateral incision was made in a cadaveric specimen and residual intervertebral disc material was removed between the L3 and L4 vertebrae. The implant was inserted in a compressed, insertion configuration into the L3 to L4 intervertebral disc space.

A first inflation device (High Pressure Inflation Device from Sis Medical) was attached to the two balloons arranged to cause anterior-posterior expansion and a second inflation device of the same type was attached to the two balloons arranged to cause cranio-caudal expansion. The implant holding and insertion instrument was detached from the implant.

Water at a pressure of between 24 and 30 bar was introduced into the two balloons arranged to cause anteroposterior expansion using the first inflation device. The anterior-posterior dimension of the implant increased without causing any increase in the cranio-caudal dimension of the implant.

Subsequently, water at a pressure of between 24 and 30 bar was introduced into the two balloons arranged to cause cranio-caudal expansion using the second inflation device. The cranio-caudal dimension of the implant increased without causing any increase in the anterior-posterior dimension of the implant. A biomechanical study of the resulting expanded implant showed that it stabilized the L3 and L4 vertebrae.

Example 2

Four separate catheter balloons (OPN NC® High Pressure PTCA Balloons from Sis Medical, having a highest rated burst pressure of 35 bar) were inserted into a bottom end of a cannulated implant holding and insertion instrument and pushed through the instrument such that part of the tubes connected to the catheter balloons were retained within the instrument but catheter balloons protruded from the top end of the instrument. The four balloons were subsequently inserted into an implant as shown in FIG. 1. The implant was mounted on the implant holding and insertion instrument using a pair of protruding blade springs which engaged with grooves on either side of the implant and retained the implant in a compressed, insertion configuration.

A lateral incision was made in a cadaveric specimen and residual intervertebral disc material was removed between the L3 and L4 vertebrae. The implant was inserted in a compressed, insertion configuration into the L3 to L4 intervertebral disc space.

A first inflation device (High Pressure Inflation Device from Sis Medical) was attached to the two balloons arranged to cause anterior-posterior expansion and a second inflation device of the same type was attached to the two balloons arranged to cause cranio-caudal expansion. The implant holding and insertion instrument was detached from the implant.

Polymethyl methacrylate (PMMA) cement in a fluid state and at a pressure of between 24 and 30 bar was introduced into the two balloons arranged to cause anterior-posterior expansion using the first inflation device. The anterior-posterior dimension of the implant increased without causing any increase in the cranio-caudal dimension of the implant.

Subsequently, PMMA cement at a pressure of between 24 and 30 bar was introduced into the two balloons arranged to cause cranio-caudal expansion using the second inflation device. The cranio-caudal dimension of the implant increased without causing any increase in the anterior-posterior dimension of the implant.

The PMMA cement was cured. After curing of the PMMA cement, the tubes attached to the balloon catheters were removed. A biomechanical study of the resulting expanded implant showed that it stabilized the L3 and L4 vertebrae.

The invention claimed is:

1. An intervertebral implant configured for insertion along a lateral insertion direction into an intervertebral space defined between a superior vertebra and an inferior vertebra, the intervertebral implant comprising:
   a first bone contacting member having a first bone contacting surface configured to face the inferior vertebra;
   a second bone contacting member spaced from the first bone contacting member along a cranial-caudal direction, the second bone contacting member having a second bone contacting surface configured to face the superior vertebra, wherein the first and second bone contacting members have respective sides that are spaced apart along an anterior-posterior direction that is substantially perpendicular to the cranial-caudal direction, wherein the anterior-posterior direction and the cranial-caudal direction are substantially perpendicular to the lateral insertion direction when the implant is disposed in the intervertebral space;
   at least two expansion compartments that are elongate along the lateral insertion direction and disposed between the first and second bone contacting surfaces, the at least two expansion compartments being spaced apart with respect to each other along the anterior-posterior direction, each expansion compartment defining a first side, a second side spaced from the first side along the anterior-posterior direction, and a distance that extends from the first side to the second side along the anterior-posterior direction, each expansion compartment configured to expand so as to increase the distance between the first and second sides, wherein each of the at least two expansion compartments are configured to cooperate with at least one of the first and second bone contacting members to cause the expansion of the implant in the anterior-posterior direction without substantially causing the implant to expand in the cranial-caudal direction.

2. The implant of claim 1, wherein the first bone contacting member comprises a first contacting component, a second contacting component spaced from the first contacting component along the anterior-posterior direction, and a first expandable connection that links the first and second contacting components, wherein the first and second contacting components define an anterior-posterior dimension that is parallel to the anterior-posterior direction,
   wherein the first and second contacting components of the first bone contacting member are arranged such that as the anterior-posterior dimension of the implant increases the first expandable connection expands and the first and second contacting components move apart relative to each other along the anterior-posterior direction.

3. The implant of claim 2, wherein the second bone contacting member comprises a third contacting component, a fourth contacting component, and a second expandable connection that links the third contacting component with the fourth contacting component.

4. The implant of claim 3, further comprising two or more additional expansion compartments.

5. The implant of claim 2, wherein the first expandable connection comprises a wire netting.

6. The implant of claim 5, wherein the wire netting comprises a plurality of individual link members.

7. The implant of claim 1, wherein the at least two expansion compartments are first and second expansion compartments, and the first and second expansion compartments are arranged parallel to each other.

8. The implant of claim 7, wherein the first and second expansion compartments are aligned with each other along the anterior-posterior direction.

9. The implant of claim 1, wherein each one of the at least two expansion compartments is an inflatable balloon.

10. The implant of claim 9, wherein the inflatable balloon is an elongated expansion balloon having a length substantially greater than an un-inflated diameter.

11. The implant of claim 10, wherein the length extends in a direction that is perpendicular to the cranial-caudal direction and the anterior-posterior direction.

12. The implant of claim 1, wherein the at least two expansion compartments are configured to expand in the cranial-caudal direction.

13. The implant of claim 1, wherein an axis that is aligned with the anterior-posterior direction extends through the at least two expansion compartments.

14. A method for implanting an intervertebral implant into an intervertebral space defined between a superior vertebra and an inferior vertebra spaced apart along a cranial-caudal direction, each vertebrae including an anterior side and a posterior side spaced from the anterior side along an anterior-posterior direction that is perpendicular to the cranial-caudal direction, the method comprising:
   inserting the intervertebral implant into the intervertebral space along a lateral insertion direction that is perpendicular to the cranial caudal direction and the anterior-posterior direction, the intervertebral implant including a first bone contacting member, a second bone contacting member spaced from the first bone contacting member along the cranial-caudal direction; and
   after the insertion step, expanding at least two expansion compartments of the intervertebral implant along the anterior-posterior direction, the at least two expansion compartments being spaced apart with respect to each other along the anterior-posterior direction, wherein during the expanding step, the at least two expansion compartments cooperate with at least one of the first and second bone contacting members to expand the intervertebral implant along the anterior-posterior direction without expanding the intervertebral implant in the cranial-caudal direction.

15. The method of claim 14, wherein the intervertebral implant is inserted along the lateral insertion direction through a lateral incision disposed laterally with respect to the superior and inferior vertebra.

16. The method of claim 14, wherein at least one of the first and second bone contacting members includes a first contacting component and a second contacting component spaced from the first contacting component along the anterior-posterior direction and defining a first dimension along the anterior-posterior direction, wherein the expanding step includes increasing the first dimension along the anterior-posterior direction.

17. The method of claim 16, further comprising an expandable connection that links the first and second contacting components, wherein the expanding step includes expanding the expandable connection.

18. The method of claim 16, wherein the expanding step includes inserting a filler material into the at least two expansion compartments.

19. The method of claim 18, wherein the at least two expansion compartments are a first expansion compartment and a second expansion compartment, wherein the expanding step includes simultaneously inserting the filler material into the first and second expansion compartments.

20. The method of claim 14, wherein each of the first and second bone contacting members includes a first end and a second end opposed to the first end, and the at least two expansion compartments are attached to the first end of the first and second bone contacting members, wherein the method further comprises detaching the at least two expansion compartments from the first ends of the first and second bone contacting members.

21. The method of claim 20, wherein each first end includes a respective fixing member, and each expansion compartment includes a hook attached to the respective fixing member, wherein the detaching step includes sliding the respective hooks off of the respective fixing members.

* * * * *